(12) United States Patent
Gray et al.

(10) Patent No.: US 9,743,831 B2
(45) Date of Patent: Aug. 29, 2017

(54) RETINAL IMAGING APPARATUS AND METHOD

(75) Inventors: Dan Gray, Fife (GB); Stephen Pemberton, Fife (GB); Derek Swan, Fife (GB); Martin Thomson, Lothian (GB)

(73) Assignee: OPTOS PLC, Dunfermline, Fife (GB)

( * ) Notice: Subject to any disclaimer, the term of this patent is extended or adjusted under 35 U.S.C. 154(b) by 0 days.

(21) Appl. No.: 13/805,604

(22) PCT Filed: Jun. 2, 2011

(86) PCT No.: PCT/GB2011/051038
§ 371 (c)(1),
(2), (4) Date: Feb. 4, 2013

(87) PCT Pub. No.: WO2012/001382
PCT Pub. Date: Jan. 5, 2012

(65) Prior Publication Data
US 2013/0135583 A1    May 30, 2013

(30) Foreign Application Priority Data
Jul. 1, 2010 (GB) .................................. 1011095.5

(51) Int. Cl.
*A61B 3/12* (2006.01)
*A61B 3/10* (2006.01)
*G02B 26/10* (2006.01)

(52) U.S. Cl.
CPC .............. *A61B 3/1025* (2013.01); *A61B 3/12* (2013.01); *A61B 3/1225* (2013.01);
(Continued)

(58) Field of Classification Search
CPC ....... A61B 3/00; A61B 3/0008; A61B 3/1025; G02B 26/0833; G02B 26/101
(Continued)

(56) References Cited

U.S. PATENT DOCUMENTS

| 4,666,269 A | 5/1987 | Nakamura et al. |
| 5,585,873 A | 12/1996 | Shalon et al. |

(Continued)

FOREIGN PATENT DOCUMENTS

| CN | 101489468 A | 7/2009 |
| GB | 2440163 A | 1/2008 |

(Continued)

OTHER PUBLICATIONS

Notification of Reasons for Refusal issued in corresponding application No. Japanese Patent Application 2013-517525 dated Jun. 30, 2015.
(Continued)

*Primary Examiner* — Zachary Wilkes
(74) *Attorney, Agent, or Firm* — Pavan Agarwal; Shabbi S. Khan; Foley & Lardner LLP

(57) ABSTRACT

The invention provides an apparatus and method for scanning, imaging and treating the retina of an eye. The apparatus (10) comprises a source of collimated light (14), a two-dimensional scanning device (16) having two axes of rotation (16a, 16b), wherein the axes of rotation (16a, 16b) are orthogonal and substantially planar, and wherein the source of collimated light (14) and the two-dimensional scanning device (16) combine to provide a two-dimensional collimated light scan from a point source (22). The apparatus (10) further comprises a scan transfer device (18), wherein the scan transfer device (18) has two foci (18a, 18b) and the point source (22) is provided at a first focus point (18a) of the scan transfer device (18) and an eye (12) is accommodated at a second focus point (18b) of the scan transfer device (18), and wherein the scan transfer device (18) transfers the two-dimensional collimated light scan from the point source (22) into the eye (12).

17 Claims, 5 Drawing Sheets

(52) U.S. Cl.
CPC ......... *G02B 26/101* (2013.01); *G02B 26/105* (2013.01); *A61B 2562/028* (2013.01)

(58) Field of Classification Search
USPC .................................................. 351/206, 220
See application file for complete search history.

(56) References Cited

U.S. PATENT DOCUMENTS

| | | | |
|---|---|---|---|
| 5,815,242 A | 9/1998 | Anderson et al. | |
| 6,244,712 B1 | 6/2001 | Smith et al. | |
| 6,288,784 B1* | 9/2001 | Hitzenberger et al. | 356/485 |
| 6,337,920 B1* | 1/2002 | Muhlhoff | A61B 3/1225 351/200 |
| 7,134,754 B2* | 11/2006 | Kerr et al. | 351/206 |
| 7,224,507 B2* | 5/2007 | Kamiya et al. | 359/290 |
| 2006/0187462 A1* | 8/2006 | Srinivasan | A61B 3/102 356/479 |
| 2007/0010313 A1 | 1/2007 | Akita | |
| 2007/0109619 A1 | 5/2007 | Eberl et al. | |
| 2007/0285793 A1 | 12/2007 | Liu et al. | |
| 2008/0151185 A1 | 6/2008 | Saito et al. | |

FOREIGN PATENT DOCUMENTS

| | | |
|---|---|---|
| JP | H08-145701 A | 6/2008 |
| JP | 2009-119173 A | 6/2009 |
| JP | 2009-543585 A | 12/2009 |
| WO | WO-2008-009877 | 1/2008 |

OTHER PUBLICATIONS

Search Report for CN201180032916 issued Jul. 9, 2014.
EP Examination Report issued in EP Application No. 11 727 746.7 dated Nov. 24, 2016.

* cited by examiner

RETINAL IMAGING APPARATUS AND METHOD

The present invention relates to an apparatus and method for scanning, imaging and treating the retina of a human eye.

Imaging systems, such as scanning laser ophthalmoscopes (SLOs), may comprise a large number of optical components, such as laser scanning elements, scan transfer mirrors, laser sources and detectors. The laser scanning arrangement consists of two separate orthogonal scanning elements, which typically include a high speed rotating polygonal mirror and a motor driven slow speed mirror. These elements are used to create a raster scan pattern of the human retina. The polygon mirror has a plurality of facets and typically provides the vertical scanning of the laser beam, and the slow speed mirror typically provides the horizontal scanning of the laser beam. The scan transfer mirror transfers the two dimensional laser scan pattern created by the scanning elements to the retina of the eye.

While such imaging systems provide acceptable images of the retina of the eye, they are limited in that they are expensive to manufacture (the laser scanning elements and scan transfer mirror are particularly expensive components), large in size and, due to the large number of optical components, have low optical efficiency According to a first aspect of the present invention there is provided an apparatus for scanning the retina of an eye comprising:

a source of collimated light;

a two-dimensional scanning device having two axes of rotation, wherein the axes of rotation are orthogonal and substantially planar, and wherein the source of collimated light and the two-dimensional scanning device combine to provide a two-dimensional collimated light scan from a point source; and the apparatus further comprises a scan transfer device, wherein the scan transfer device has two foci and the point source is provided at a first focus point of the scan transfer device and an eye is accommodated at a second focus point of the scan transfer device, and wherein the scan transfer device transfers the two-dimensional collimated light scan from the point source into the eye.

One of the two axes of rotation of the two-dimensional scanning device may be perpendicular to a line joining the two foci of the scan transfer device. In this arrangement, given that the two axes of rotation of the scanning device are orthogonal, when one of the two axes of rotation of the two-dimensional scanning device is perpendicular, or parallel, to a line joining the two foci of the scan transfer device, the other of the two axes of rotation is parallel, or perpendicular, to the line joining the two foci of the scan transfer device.

The scanning device may be configured to rotate about one of the two axes of rotation at a faster or slower speed than the other of the two axes of rotation.

The scanning device may comprise a one-dimensional scanning element having a first axis of rotation and a rotatable mount having a second axis of rotation orthogonal to the first axis, and wherein the one-dimensional scanning element is mounted to the rotatable mount. In this arrangement, the scanning device, together with the source of collimated light, provides a two-dimensional collimated light scan from a point source. In this arrangement, the rotational axis of the rotatable mount may be separated slightly from the rotational axis of the one-dimensional scanning element, such that the rotational axes lie on slightly separated planes. This ensures that the collimated light emanates from a point source.

The axis of rotation of the one-dimensional scanning element may be perpendicular or parallel to the line joining the two foci of the scan transfer device.

The axis of rotation of the rotatable mount may be perpendicular or parallel to the line joining the two foci of the scan transfer device.

In this arrangement, given that the two axes of rotation of the one-dimensional scanning element and rotatable mount are orthogonal, when one of the axes of the one-dimensional scanning element or rotatable mount is perpendicular, or parallel, to the line joining the two foci of the scan transfer device, the other of the axes of the one-dimensional scanning element or rotatable mount is parallel, or perpendicular to the line joining the two foci of the scan transfer device.

The one-dimensional scanning element may be configured to rotate about its axis of rotation at a faster speed than the speed at which the rotatable mount rotates about its axis. Alternatively, the one-dimensional scanning element may be configured to rotate about its axis of rotation at a slower speed than the speed at which the rotatable mount rotates about its axis.

The one-dimensional scanning element may be an oscillating mechanism, an oscillating mirror, a resonant scanner, a resonant scanning mirror, a microelectromechanical system (MEMS) scanning element, or a rotating polygon.

The rotatable mount may include a mounting portion for the one-dimensional scanning element and a shaft portion, wherein the mounting portion is located at the end of the shaft. The rotation of the mount may be mechanically driven. The shaft portion may be mechanically driven. The rotation of the mount may be automated. The rotation of the mount may be computer-controlled.

The two-dimensional scanning device may be configured to rotate about one of its two axes of rotation at a faster or slower speed than the other of its two axes of rotation.

The two-dimensional scanning device may be a microelectromechanical system (MEMS) scanning element. However, it should be appreciated that the two-dimensional scanning device may be any suitable device which is capable of rotating in at least two axes, which are preferably orthogonal. The scanning device should preferably be capable of operating at high speed (i.e. above 5 kHz) and provide a high amplitude of scan (i.e. up to 180 degrees or more).

The scanning device may have operating parameters which are selected to control the direction of the two-dimensional collimated light scan from the point source and/or adjust the dimensions of the two-dimensional collimated scan from the point source.

Selecting the operating parameters of the scanning device to control the direction of the two-dimensional collimated light scan and/or adjust the dimensions of the two-dimensional collimated light scan allows the size of the area and position of the scan on the retina to be controlled. For example, the scanning device may be configured to produce a "maximum area" two-dimensional collimated light scan. The operating parameters may then be selected to adjust the horizontal/vertical dimensions of the scan such that a "smaller area" scan may be produced at any point within the "maximum area" scan. This effectively allows the "smaller area" scan to be "moved" across the retina within the "maximum area" by an appropriate selection of the operating parameters to build up a montage of high resolution images of the retina.

Depending on the scanning device used, the operating parameters can be selected to control the direction of the two-dimensional collimated light scan from the point source and/or adjust the dimensions of the two-dimensional collimated light scan from the point source. For example, if the scanning device includes rotating, or oscillating, elements, the direction of the two-dimensional collimated light scan from the point source can be controlled.

Importantly, the two-dimensional collimated light scan always emanates from the point source, regardless of the selected operating parameters of the scanning device.

The operating parameters of the scanning device may include the amplitude of the oscillation and the rotational offset of the oscillation. The operating parameters of the scanning device may also include the velocity of the oscillation.

The scan transfer device may comprise an aspherical mirror, an elliptical mirror, an ellipsoidal mirror, a pair of parabola mirrors or a pair of paraboloidal mirrors.

The source of collimated light may be a laser, a light emitting diode (LED), a Vertical Cavity Surface Emitting Laser (VCSEL), a super luminescent diode, a diode laser or a collimated incandescent lamp.

Each source of collimated light may be adapted to provide light at a wavelength between 450 nmm and 1000 nmm. Preferably, the source of collimated light may be adapted to provide light at a wavelength between 488 nmm and 700 nmm. More preferably, the source of collimated light provides light at a wavelength of between 515 nmm and 650 nm.

The source of collimated light may be adapted to provide light at a power of between 500 nWatt and 1 W.

The source of collimated light may include one or more light sources of differing wavelengths.

The source of collimated light may be configured such that the wavelength of light provided is variable.

The source of collimated light may be configured such that the power of light provided is variable.

The apparatus may be pivotable between a first position, in which the apparatus may be used to scan the first retina of a first eye, and a second position, in which the apparatus may be used to scan the second retina of a second eye.

The apparatus may further comprise a light detector for detecting light reflected from the retina to produce an image of the retina. In this arrangement the apparatus scans the retina and obtains an image of the scanned part of the retina.

The light detector may include fast photo detectors, such as avalanche photo diodes (APDs), PIN diodes, photomultiplier tubes (PMT), silicon photo multipliers (SPM), or similar single point detectors.

The apparatus may further comprise one or more data processing devices for displaying, storing and/or combining the obtained images of the retina.

According to a second aspect of the present invention, there is provided a system for scanning the retina of each eye of a patient comprising two apparatuses according to the first aspect of the invention, wherein each apparatus may be capable of scanning the retina of one eye.

According to a third aspect of the present invention there is provided a method of scanning the retina of an eye comprising the steps of:
  providing a source of collimated light;
  providing a two-dimensional scanning device having two axes of rotation, wherein the axes of rotation are orthogonal and substantially planar;
  using the source of collimated light and the two-dimensional scanning device in combination to provide a two-dimensional collimated light scan from a point source;
  providing a scan transfer device having two foci;
  providing the point source at a first focus point of the scan transfer device and an eye at the second focus point of the scan transfer device; and
  using the scan transfer device to transfer the two-dimensional collimated light scan from the point source into the eye.

The source of collimated light may be configured such that the wavelength of light provided is variable and the method may include the further step of varying the wavelength of light from the source.

The source of collimated light may be configured such that the power of light provided is variable and the method may include the further step of varying the power of light from the source.

The method may comprise the further step of providing a light detector and using the light detector to detect light reflected from the retina to produce an image of the retina. In this arrangement the method performs the steps of scanning the retina and obtaining an image of the scanned retina.

According to a fourth aspect of the present invention there is provided an apparatus for imaging the retina of an eye comprising:
  a source of collimated light;
  a light detector;
  a two-dimensional scanning device having two axes of rotation, wherein the axes of rotation are orthogonal and substantially planar, and wherein the source of collimated light and the two-dimensional scanning device combine to provide a two-dimensional collimated light scan from a point source; and
  the apparatus further comprises a scan transfer device, wherein the scan transfer device has two foci and the point source is provided at a first focus point of the scan transfer device and an eye is accommodated at a second focus point of the scan transfer device, and wherein the scan transfer device transfers the two-dimensional collimated light scan from the point source into the eye and the light detector detects light reflected from the retina to obtain an image of the retina.

According to a fifth aspect of the present invention there is provided an apparatus for treating the retina of an eye with collimated light comprising:
  a source of collimated light;
  a two-dimensional scanning device having two axes of rotation, wherein the axes of rotation are orthogonal and substantially planar, and wherein the source of collimated light and the two-dimensional scanning device combine to provide a two-dimensional collimated light scan from a point source; and
  the apparatus further comprises a scan transfer device, wherein the scan transfer device has two foci and the point source is provided at a first focus point of the scan transfer device and an eye is accommodated at a second focus point of the scan transfer device, and wherein the scan transfer device transfers the two-dimensional collimated light scan from the point source into the eye.

Treatment of the retina is interpreted here to include photodynamic therapy, photo-ablation, photoporation, photoactivation or other methods where the interaction of the light is used to alter the state or structure of the retina or to alter the state of chemicals within the retinal structure.

According to a sixth aspect of the present invention there is provided a method of imaging the retina of an eye comprising the steps of:
  providing a source of collimated light;
  providing a light detector;
  providing a two-dimensional scanning device having two axes of rotation, wherein the axes of rotation are orthogonal and substantially planar;
  using the source of collimated light and the two-dimensional scanning device in combination to provide a two-dimensional collimated light scan from a point source;
  providing a scan transfer device having two foci;
  providing the point source at a first focus point of the scan transfer device and an eye at the second focus point of the scan transfer device;
  using the scan transfer device to transfer the two-dimensional collimated light scan from the point source into the eye; and
  using the light detector to detect light reflected from the retina to produce an image of the retina.

According to a seventh aspect of the present invention there is provided a method of treating the retina of an eye with collimated light comprising the steps of:
  providing a source of collimated light;
  providing a two-dimensional scanning device having two axes of rotation, wherein the axes of rotation are orthogonal and substantially planar;
  using the source of collimated light and the two-dimensional scanning device in combination to provide a two-dimensional collimated light scan from a point source;
  providing a scan transfer device having two foci;
  providing the point source at a first focus point of the scan transfer device and an eye at the second focus point of the scan transfer device; and
  using the scan transfer device to transfer the two-dimensional collimated light scan from the point source into the eye.

Treatment of the retina is interpreted here to include photodynamic therapy, photo-ablation, photoporation, photoactivation or other methods where the interaction of the light is used to alter the state or structure of the retina or to alter the state of chemicals within the retinal structure.

Embodiments of the present invention will now be described, by way of example only, with reference to the accompanying drawings, in which.

Figure 1:
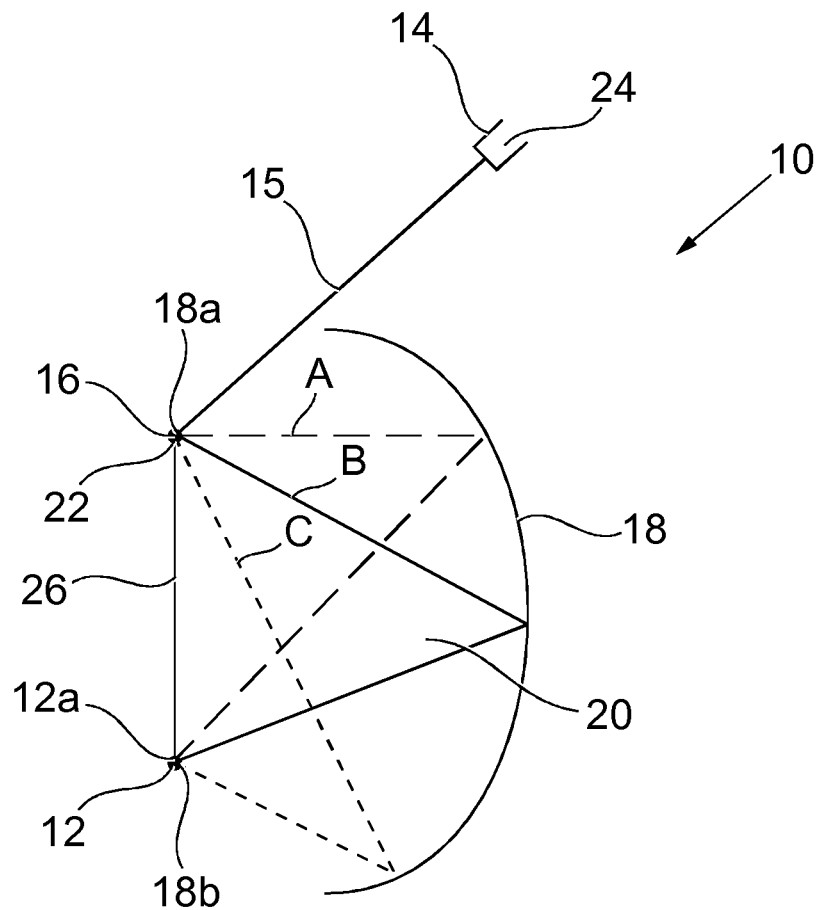
FIG. 1 is a simplified optical schematic side view of an apparatus for scanning, imaging and treating the retina of an eye according to the present invention.
Figure 2:
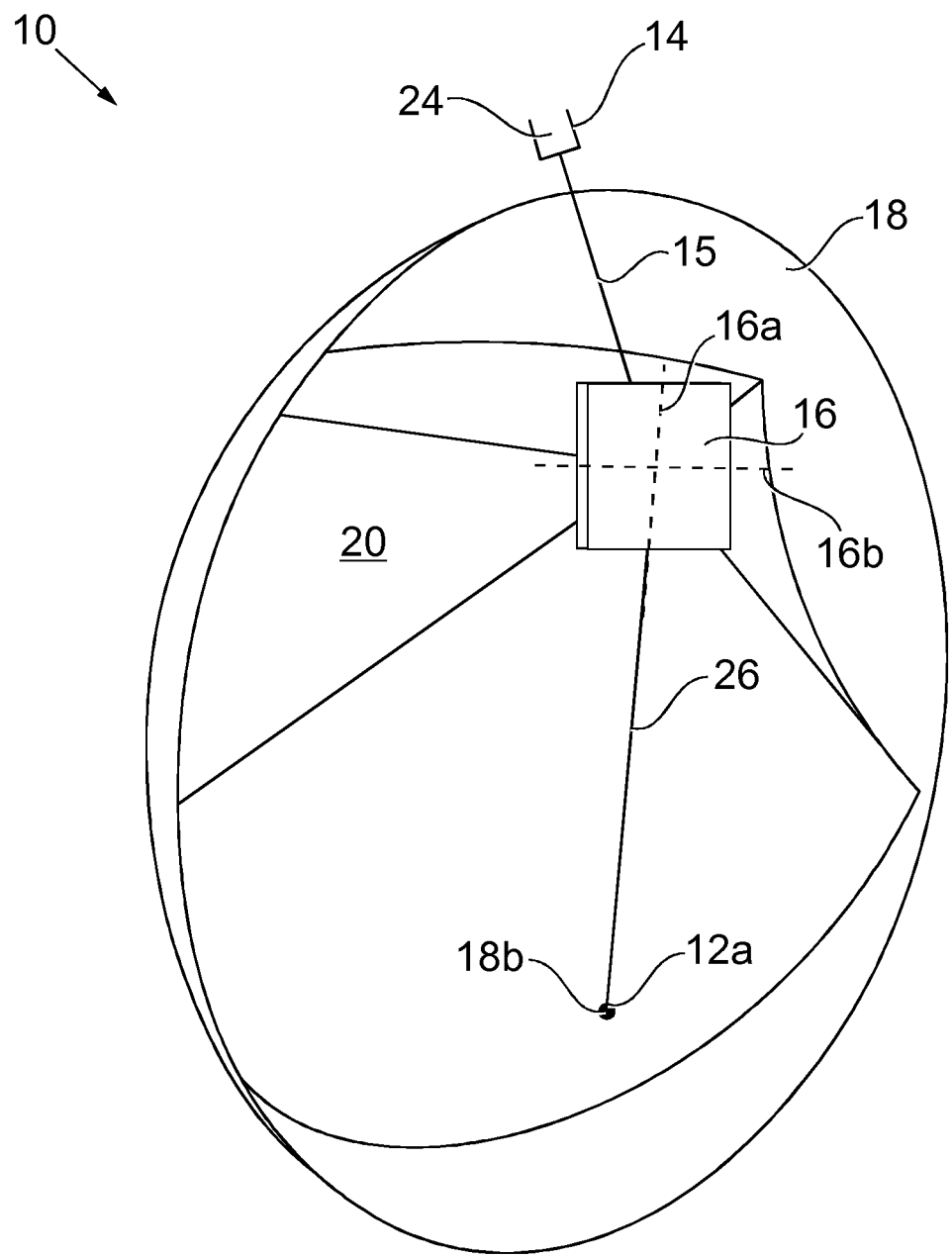
FIG. 2 is a rear perspective view of apparatus of FIG. 1.
Figure 3:
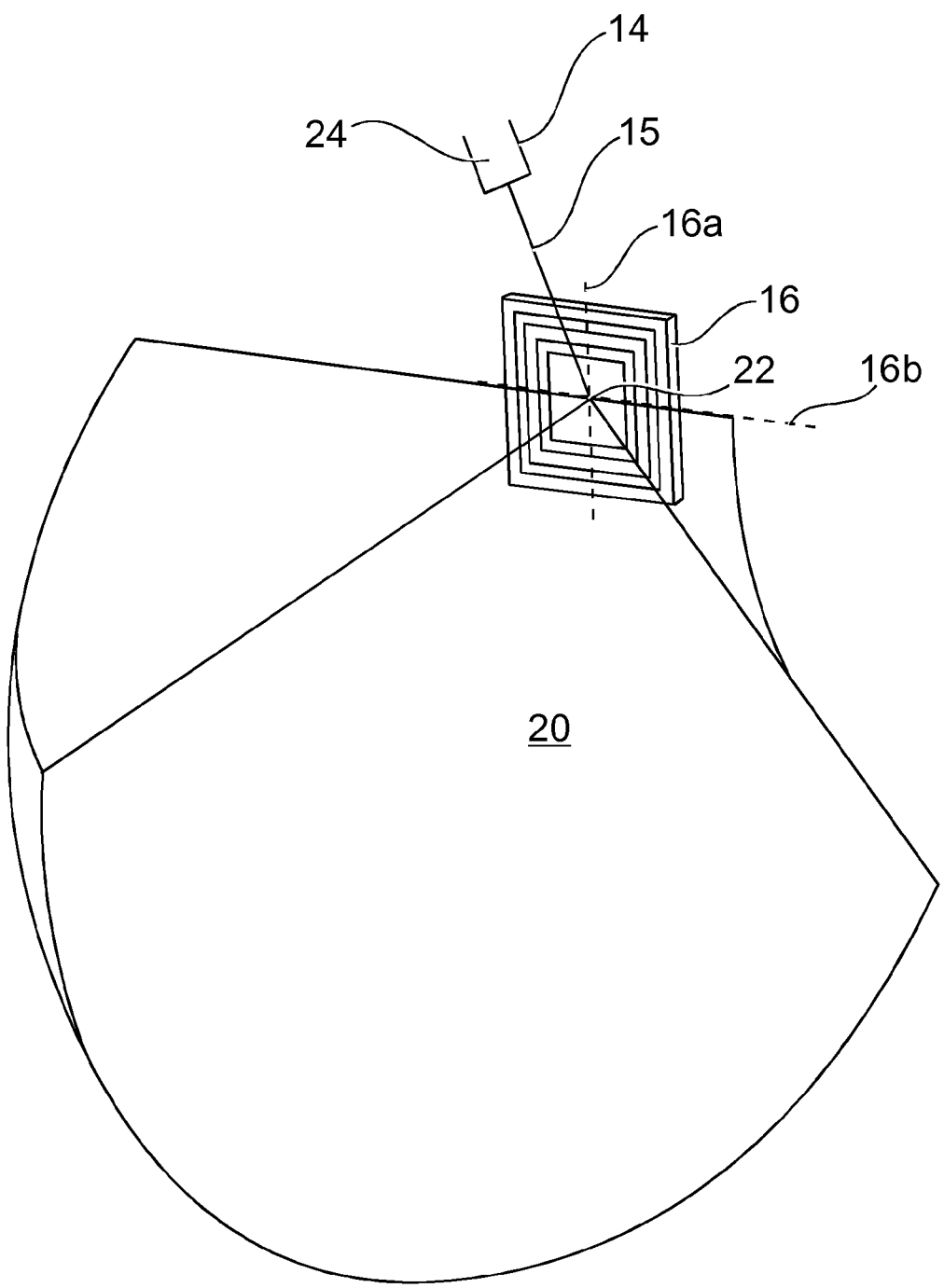
FIG. 3 is a front perspective view of the two-dimensional scanning device of FIG. 2.

FIGS. 1 to 3 illustrate an apparatus 10 for scanning the retina of an eye 12. The apparatus 10 includes a source of collimated light 14, a two-dimensional scanning device 16 and a scan transfer device 18.

The source of collimated light 14 in the embodiment described here is a diode laser. However, it should be appreciated that any suitable source of collimated light could be used, such as Vertical Cavity Surface Emitting Laser (VCSEL), a super luminescent diode (SLD), a collimated incandescent lamp, or another source that has enough intensity and spatial coherence to be well collimated and produce adequate retinal illumination. The source of collimated light 14 produces a laser beam 15.

The source of collimated light 14 may be adapted to provide light between the wavelength of 450 nmm and 1000 nmm. Preferably, the source of collimated light 14 provides light at a wavelength of between 515 nmm and 650 nmm. The source of collimated light 14 may also be able to provide light at a number of different wavelengths. In this arrangement the source of collimated light 14 may include a number of light sources. Also, the source of collimated light 14 may be adapted such that the wavelength of collimated light produced may be varied.

The source of collimated light 14 may also be adapted to provide light at a power of between 500 nW and 1 W. Also, the source of collimated light 14 may be adapted such that the power of the collimated light may be varied.

The two-dimensional scanning device 16 has two axes of rotation 16a, 16b (see FIGS. 2 and 3). The axes of rotation 16a, 16b are orthogonal and lie in the same plane.

With reference to FIGS. 1 and 2, the source of collimated light 14 directs the laser beam 15 towards the two-dimensional scanning device 16. The scanning device 16 reflects the laser beam 15 towards the scan transfer device 18.

As the laser beam 15 is reflected from the scanning device 16, the scanning device 16 is rotated about its axes 16a, 16b. The rotation of the scanning device 16 about its axes 16a, 16b is controlled to produce a raster scan of the collimated light.

Thus, a two-dimensional collimated light scan 20 is produced which emanates from a point source 22. As illustrated in FIG. 3, the point source 22 lies on the surface of the scanning device 16. The scanning device 16 is rotated about its axes 16a, 16b such that the point source 22 remains stationary. The path of the laser beam 15 during rotation of one of the axes 16a, 16b is illustrated in FIG. 1. Path A is an example of the laser beam 15 reflected from the scanning device 16 at the start of the rotation; path B is an example of the laser beam 15 reflected from the scanning device 16 at an intermediate point of the rotation; and path C is an example of the laser beam 15 reflected from the scanning device 16 at the end of the rotation.

The two-dimensional scanning device 16 is a microelectromechanical system (MEMS) scanning element. However, it should be appreciated that the scanning device 16 could be any suitable device which is able generate a two-dimensional collimated light scan from a point source. The scanning device should preferably be capable of operating at high speed (i.e. above 5 kHz) and provide a high amplitude of scan (i.e. up to 180 degrees or more).

The scanning device 16 has operating parameters which include the amplitude of oscillation and the rotational offset of the oscillation along each axis 16a and 16b. Both of these operating parameters may be selected to control the direction of the two-dimensional collimated light scan 20 from the point source 22 and/or adjust the dimensions of the two-dimensional collimated light scan 20 on the scan transfer device 18, and thus on the retina (see below). This provides the ability to "move" the imaging field of the two-dimensional collimated light scan 20 across the retina (see below). The operating parameters also include the velocity of rotation.

The scan transfer device 18 has two foci; a first foci 18a and a second foci 18b. In the embodiment described here the scan transfer device 18 is an ellipsoidal mirror. However, it should be appreciated that the scan transfer device 18 may alternatively be an aspherical mirror, an elliptical mirror, a pair of parabola mirrors or a pair of paraboloidal mirrors.

As best illustrated in FIG. 1, the apparatus 10 is arranged such that the point source 22 is positioned at the first focus point 18a of the scan transfer device 18 and the eye 12 is positioned at the second focus point 18b of the scan transfer device 18b. More specifically, the pupillary point 12a of the eye 12 is positioned at the second focus point 18b of the scan transfer device 18b.

The laser beam 15 is conveyed to the subject's eye 12 via the two-dimensional scanning device 16 and the scan transfer device 18. The two-dimensional collimated light scan 20 provided at the point source 22 by the source of collimated light 14 and the two-dimensional scanning device 16 is coupled by the scan transfer device 18 through the pupillary point 12a of the subject's eye 12, and thus onto the retina. Thus, the apparatus 10 provides a two-dimensional collimated light scan 20 on the retina.

As stated above, the two-dimensional scanning device 16 is arranged such that the point source 22 is stationary during operation, which, due to the properties of the scan transfer device 18, means that the two-dimensional collimated light scan 20 emerging at the second focus point 18b of the scan transfer device 18 is also stationary. That is, the scan transfer device 18 provides point-to-point transfer, without introducing any translation component to the two-dimensional collimated light scan 20.

Since the two-dimensional collimated light scan 20 emerging at the second focus point 18b of the scan transfer device 18 has no axial translation, the "full" scan may enter the eye. That is, the scan is not "clipped" by the iris, for example. This maximises the area of the retina that can be scanned by the apparatus 10 and allows ultra wide field imaging to be performed. Similarly, since the pupillary point 12a of the eye 12 is positioned at the second focus point 18b of the scan transfer device, this also prevents clipping of the two-dimensional collimated light scan 20 by the iris and again ensures that the full scan enters the eye to maximise the area of the retina that can be scanned by the apparatus 10.

A stationary point source 22 also ensures that the reflected collimated light from the retina is conveyed back through the same optical path of the apparatus 10. The reflected collimated light is detected at a detector 24. The reflected collimated light is used to produce an image of the subject's retina in the known manner. Although the detector 24 is illustrated in FIG. 1 as being located with the source of collimated light 14, it should be appreciated that the detector 24 may be located separately from the source of collimated light 14 and a beam splitter may be used to divert the reflected collimated light from the optical path to the detector in the known manner.

As described above, the scanning device 16 has operating parameters which may be selected to control the direction of the two-dimensional collimated light scan 20 and/or adjust the dimensions of the two-dimensional collimated light scan 20 from the point source 22.

Selecting the operating parameters of the scanning device 16 to control the direction of the two-dimensional collimated light scan 20 and/or adjust the dimensions of the two-dimensional collimated light scan 20 allows the size of the area and position of the scan on the retina to be controlled. For example, the scanning device may be configured to produce a "maximum area" two-dimensional collimated light scan 20. The operating parameters may then be selected to adjust the horizontal/vertical dimensions of the scan such that a "smaller area" scan may be produced at any point within the "maximum area" scan. This effectively allows the "smaller area" scan to be "moved" across the retina within the "maximum area" by an appropriate selection of the operating parameters to build up a montage of images of the retina.

In the embodiment described and illustrated here the axis of rotation 16b of the two-dimensional scanning device 16 is perpendicular to a line 26 joining the two foci 18a, 18b of the scan transfer device 18. In this arrangement, given that the two axes of rotation 16a, 16b are orthogonal, the axis of rotation 16a is parallel to the line 26 joining the two foci 18a, 18b of the scan transfer device 18.

The two-dimensional scanning device 16 is configured to rotate about one of the two axes of rotation 16a, 16b at a faster or slower speed than the other of the two axes of rotation 16a, 16b. In the arrangement illustrated here the scanning device 16 is configured to rotate about the axis 16b at a faster rate than it rotates about the axis 16a. The result of this is that the "fast scan" is performed along the "low" aberration axis of the scan transfer device 18 (i.e. along the line 26 joining the two foci 18a, 18b) and the "slow scan" is performed along the relatively higher aberration axis of the scan transfer device 18. The advantage of this is that active focal correction may be performed very easily to produce an improved off axis aberration performance.

The apparatus 10 also includes a computer (not shown), or the like, for controlling the operation of the source of collimated light 14, the scanning device 16 and the detector 24. The apparatus 10 also includes at least one data processing device (not shown), such as a computer, for storing the images of retina.

Figure 4:
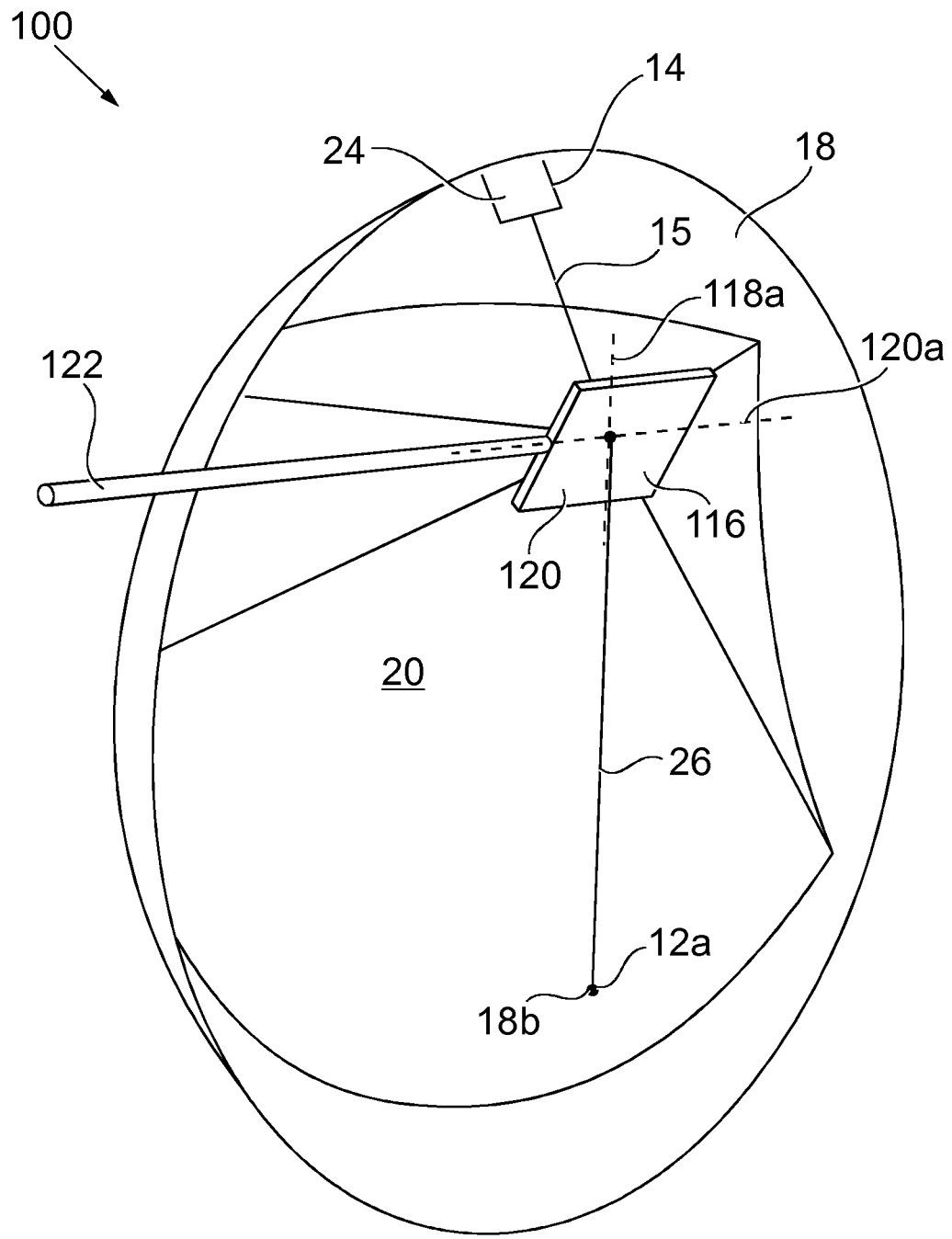
FIG. 4 is a rear perspective view of an alternative apparatus.
Figure 5:
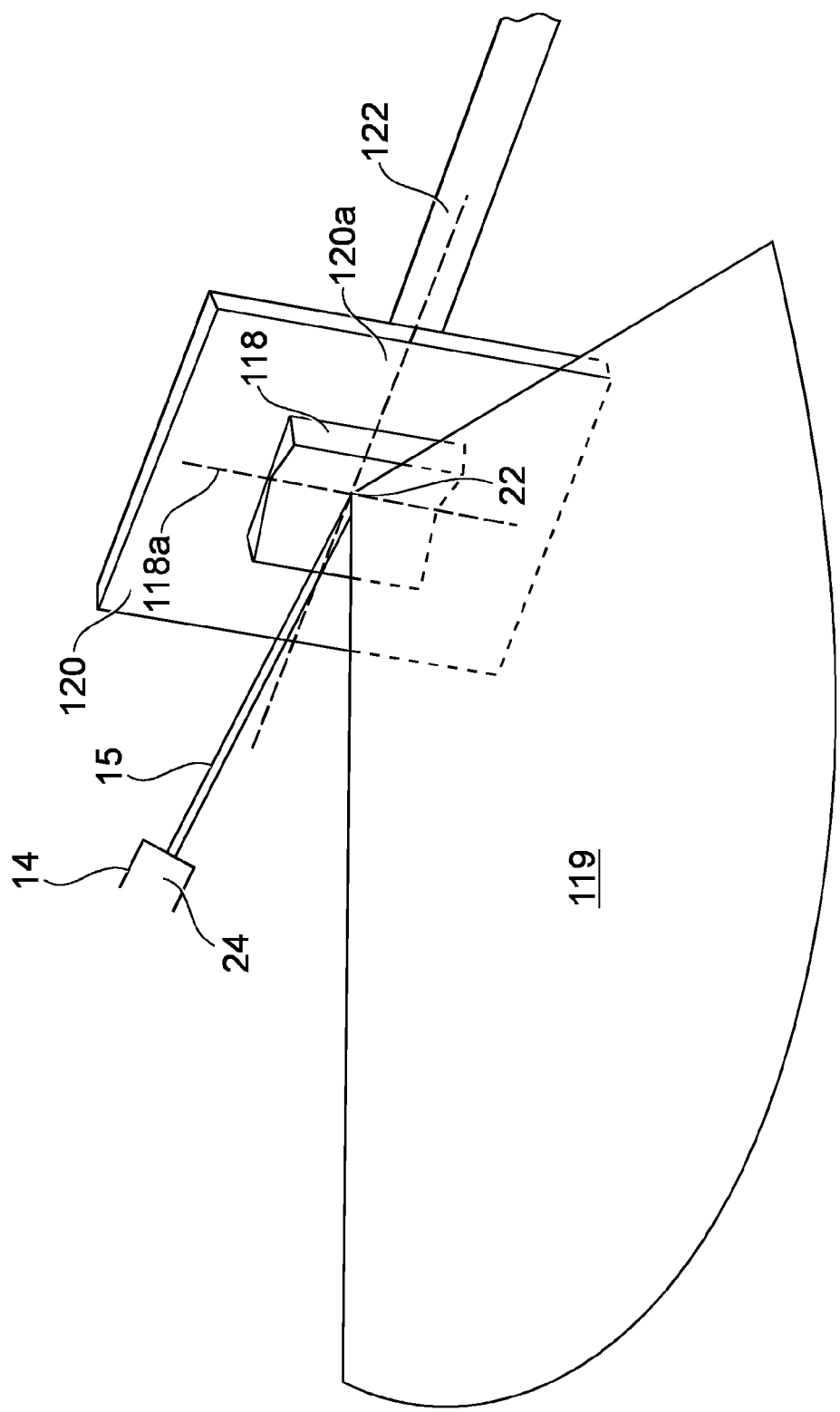
FIG. 5 is a front perspective view of the two-dimensional scanning device of FIG. 4.

FIGS. 4 and 5 illustrate an alternative embodiment of the apparatus 10. The only difference between this embodiment and the first embodiment is that the two-dimensional scanning device 116 is different to the two-dimensional scanning device 16 of the first embodiment, all other components remain unchanged.

The two-dimensional scanning device 116 comprises a one-dimensional scanning element 118 having a first axis of rotation 118a and a rotatable mount 120 having a second axis of rotation 120a. As best illustrated in FIG. 5, the one-dimensional scanning element 118 is mounted to the rotatable mount 120. The axes of rotation 118a, 120a are orthogonal and lie substantially on the same plane.

The one-dimensional scanning element 118 produces a one-dimensional collimated light scan 119 (see FIG. 5).

The two-dimensional scanning device 116 and the source of collimated light 14 again provide a two-dimensional collimated light scan 20 from a point source 22. In this arrangement, the rotational axis 120a of the rotatable mount 120 may be separated very slightly from the rotational axis 118a of the one-dimensional scanning element 118, such that the rotational axes 118a, 120a lie on slightly separated planes. This ensures that the two-dimensional collimated light scan 20 emanates from a point source 22.

As illustrated in FIG. 4, the rotational axis 120a of the rotatable mount 120 is perpendicular to the line 26 joining the two foci 18a, 18b of the scan transfer device 18. Again, given that the two axes of rotation 118a, 120a of the one-dimensional scanning element 118 and the rotatable mount 120 are orthogonal, the rotational axis 118a of the one-dimensional scanning element 118 is parallel to the line 26 joining the two foci 18a, 18b of the scan transfer device 18.

Again, the two-dimensional scanning device 116 is configured to rotate about one of the two axes of rotation 118a, 120a at a faster or slower speed than the other of the two axes of rotation 118a, 120a. In the arrangement illustrated here the scanning device 116 is configured to rotate about the axis 120a at a faster rate than it rotates about the axis 118a. The result of this is that the "fast scan" is again performed along the "low" aberration axis of the scan transfer device 18 and the "slow scan" is again performed along the relatively higher aberration axis of the scan transfer device 18. Again, the advantage of this is that active focal correction may be performed very easily to produce an improved off axis aberration performance.

In the embodiment illustrated and described here the one-dimensional scanning element 118 is a MEMS scanner. However, it should be appreciated that the one-dimensional scanning element 118 may be an oscillating mechanism, an oscillating mirror, a resonant scanner, a resonant scanning mirror, or a rotating polygon.

As best illustrated in FIG. 5, the rotatable mount 120 includes a shaft portion 122. The rotation of the shaft portion 122 may be mechanically driven. The rotation of the shaft portion 122 may be automated and may be controlled by a computer (not shown), or the like.

The operation of the apparatus 100 is generally identical to that of the first embodiment, with the two-dimensional collimated light scan 20 entering the pupillary point 12a of the eye 12 and scanning the eye 12 in the same manner as described above.

Although the apparatus 10, 100 have been illustrated and described above as being used to scan and image the retina of a single eye 12 of a subject, it should be appreciated that the apparatus 10 may be pivotable between a first position, in which the apparatus 10, 100 may be used to scan the first retina of a first eye, and a second position, in which the apparatus 10, 100 may be used to scan the second retina of a second eye. In this arrangement the apparatus 10, 100 may be used to scan both eyes of a subject without the need to move the patient. Alternatively, there may be provided a system for scanning the retina of each eye, whereby the system comprises two apparatuses 10, 100, with each apparatus 10, 100 being used to scan an eye of the subject.

Although the apparatus 10, 100 has been described above as being used to scan the retina of the eye 12 with collimated light to obtain an image of the retina, it should be appreciated that the apparatus 10, 100 may not necessarily need to produce an image of the retina. That is, the apparatus 10, 100 may be used to simply scan collimated light across the retina without acquiring an image, i.e. not detecting the reflected light from the retina. Thus, the apparatus 10, 100 may simply illuminate the retina with collimated light.

The apparatus 10, 100 may therefore be used to treat the retina of the eye by illuminating the retina with collimated light. In this arrangement, the source of collimated light 14 may be operated to produce a laser beam of variable wavelength and/or power. Furthermore, the source of collimated light 14 may be operated to produce a number of differing wavelengths, if required. This allows the apparatus 10, 100 to treat retinal diseases.

The apparatus 10, 100 of the present invention can be manufactured at a lower cost than known retinal imaging apparatuses, such as scanning laser ophthalmoscopes (SLOs), as the apparatus 10, 100 does not require conventional separated laser scanning elements (i.e. two separate one-dimensional scanning elements separated in space from one another, such as a horizontal scanning polygon mirror and a vertical scanning galvanometer scanner). The apparatus 10, 100 can be made more compact than known retinal imaging apparatuses, since the apparatus 10, 100 uses a smaller number of components. The apparatus 10, 100 of the present invention also includes a smaller number of optical surfaces, which increases the optical efficiency of the apparatus 10, 100. The result of this is that, for the same amount of input power to the eye, the total power at the imaging detector is higher than known methods. Also, the apparatus 10, 100 may be capable of performing "wide field" imaging or "narrow field" imaging. Therefore, the apparatus 10, 100 is scalable for different markets. Furthermore, depending on the geometry of the scan transfer device 18, no focal correction is necessary to achieve high resolution imaging. This yields higher resolution images than known methods.

Modifications and improvements may be made to the above without departing from the scope of the present invention. For example, although the apparatus 10, 100 has been illustrated and described above as having two orthogonal axes of rotation, it should be appreciated that the apparatus 10, 100 may have more than two axes of rotation. In this case, the scanning pattern may not necessarily be in the form of a raster scan.

Furthermore, although the point source 22 has been illustrated and described as being coincident with the pupillary point 12a of the eye 12, it should be appreciated that the point source 22 could be located generally around the front nodal point of the eye 12. That is, the point source 22 could be located on the optical axis of the eye in front of the lens, in the plane of the iris, or at the rear nodal point of the eye 12. In order to achieve the widest field of view, i.e. to avoid clipping of the light beam, the point source 22 should be located at the front lens of the eye 12, i.e. in the plane of the iris. The point source 22 should therefore be within +/−4 mm of the plane of the iris.

It should also be appreciated that the apparatus 10, 100 may also be used for fluorescence imaging by imaging at one wavelength and detecting at another wavelength, as is common in applications such as angiography and autofluorescence imaging. It should therefore be appreciated that the apparatus 10, 100 may obtain an image of the retina by receiving light reflected from the retina or fluorescent light emitted by the retina on excitation thereof.

Also, although the apparatus 10, 100 has been described above as for illuminating and imaging the retina of the eye 12, it should be appreciated that the apparatus 10, 100 may also be used to administer treatment to the retina by illuminating the retina with collimated light of a suitable wavelength and/or power. Treating the retina may include the following steps: (i) identifying a region of the retina for treatment, (ii) specifying the size of the treatment area through treatment planning, linked to an imaging system and (iii) guiding the treatment either through manual control or pre-specified automated control to deliver the treatment illumination to single or multiple sites via a common input path to the imaging source(s). This provides a correlation between the treatment geography and treatment planning derived from the imaging system. Treating the retina may also include the optional steps of viewing an image of the retina during the treatment and/or re-imaging the retina to confirm the treatment is successful.

That is, the present invention also provides an apparatus for illuminating the retina with collimated light for use in treating the retina. The present invention also provides a method for illuminating the retina with collimated light for use in treating the retina.

The invention claimed is:

1. An apparatus for imaging the retina of an eye comprising:
a source of collimated light;
a light detector; and a two-dimensional scanning device comprising a one-dimensional scanning element having a first axis of rotation and a rotatable mount having a second axis of rotation, and wherein the one-dimensional scanning element is mounted to the rotatable mount and the first and second axes of rotation are orthogonal and substantially co-planar;

wherein the two-dimensional scanning device is arranged to receive collimated light from the source of collimated light and the source of collimated light and the two-dimensional scanning device combine in operation to provide a two-dimensional collimated light scan from a point source located at the intersection of the first and second axes; and the apparatus further comprises a scan transfer device, wherein the scan transfer device has a reflective surface, and wherein the reflective surface has a first focus point and a second focus point, and the point source is provided at the first focus point such that, in operation, the scan transfer device receives collimated light from the point source and transfers the two-dimensional collimated light scan from the point source into an eye accommodated at the second focus point, and the light detector detects light reflected from the retina of the eye to produce an image of the retina and wherein the axis of rotation of the one-dimensional scanning element is perpendicular or parallel to a line joining the first focus point and the second focus point of the scan transfer device and the axis of rotation of the rotatable mount is perpendicular or parallel to the line joining the first focus point and the second focus point of the scan transfer device.

2. An apparatus according to claim 1, wherein one of the first and second axes of rotation of the two-dimensional scanning device is perpendicular to a line joining the first focus point and the second focus point of the scan transfer device.

3. An apparatus according to claim 1, wherein the one-dimensional scanning element is one of the group comprising an oscillating mechanism, an oscillating mirror, a resonant scanner, a resonant scanning mirror, a microelectromechanical system (MEMS) scanning element and a rotating polygon.

4. An apparatus according to claim 1, wherein the rotatable mount includes a mounting portion for the one-dimensional scanning element and a shaft portion, wherein the mounting portion is located at the end of the shaft portion.

5. An apparatus according to claim 1, wherein the scanning device is configured to rotate about one of the two axes of rotation at a faster or slower speed than the other of the two axes of rotation.

6. An apparatus according to claim 1, wherein the one-dimensional scanning element is a microelectromechanical system (MEMS) scanning element.

7. An apparatus according to claim 1, wherein the scanning device has operating parameters which are selected to control the direction of the two-dimensional collimated light scan from the point source or adjust the dimensions of the two-dimensional collimated scan from the point source or both control the direction and adjust the dimensions of the two-dimensional collimated scan from the point source.

8. An apparatus according to claim 7, wherein the operating parameters of the scanning device includes at least one of the group comprising the amplitude of the oscillation, the rotational offset of the oscillation and the velocity of the oscillation.

9. An apparatus according to claim 1, wherein the source of collimated light includes one or more light sources of differing wavelengths.

10. An apparatus according to claim 1, wherein the wavelength and/or power of collimated light are variable.

11. An imaging apparatus according to claim 1, wherein in operation the scan transfer device transfers the reflected light from the eye to the two-dimensional scanning device, and the two-dimensional scanning device directs the reflected light to the light detector.

12. A method of imaging the retina of an eye comprising the steps of:
providing a source of collimated light;
providing a light detector;
providing a two-dimensional scanning device comprising a one-dimensional scanning element having a first axis of rotation and a rotatable mount having a second axis of rotation, and wherein the one-dimensional scanning element is mounted to the rotatable mount and the first and second axes of rotation are orthogonal and substantially co-planar, the two-dimensional scanning device, in use, receiving collimated light from the source of collimated light;
using the source of collimated light and the two-dimensional scanning device in combination to provide a two-dimensional collimated light scan from a point source located at the intersection of the first and second axes;
providing a scan transfer device with a reflective surface, the reflective surface having a first focus point and a second focus point;
providing the point source at the first focus point of the scan transfer device and an eye at the second focus point of the scan transfer device, the scan transfer device, in use, receiving collimated light from the point source;
using the scan transfer device to transfer the two-dimensional collimated light scan from the point source into the eye; and
detecting light reflecting from the retina to produce an image of the retina, wherein the axis of rotation of the one-dimensional scanning element is perpendicular or parallel to a line joining the first focus point and the second focus point of the scan transfer device and the axis of rotation of the rotatable mount is perpendicular or parallel to the line joining the first focus point and the second focus point of the scan transfer device.

13. A method according to claim 12, wherein the source of collimated light is configured such that the wavelength of light provided is variable and the method includes the further step of varying the wavelength of light from the source.

14. A method according to claim 12, wherein the source of collimated light is configured such that the power of light provided is variable and the method includes the further step of varying the power of light from the source.

15. A method according to claim 12, comprising using the scan transfer device to transfer the reflected light from the eye to the two-dimensional scanning device, and using the two-dimensional scanning device to direct the reflected light to the light detector.

16. An apparatus for treating the retina of an eye with collimated light, the apparatus comprising:
a source of collimated light;
a light detector; and
a two-dimensional scanning device comprising a one-dimensional scanning element having a first axis of rotation and a rotatable mount having a second axis of rotation, and wherein the one-dimensional scanning element is mounted to the rotatable mount and the first and second axes of rotation are orthogonal and substantially co-planar;

wherein the two-dimensional scanning device is arranged to receive collimated light from the source of collimated light and the source of collimated light and the two-dimensional scanning device combine in operation to provide a two-dimensional collimated light scan from a point source located at the intersection of the first and second axes; and the apparatus further comprises a scan transfer device, wherein the scan transfer device has a reflective surface, and wherein the reflective surface has a first focus point and a second focus point and the point source is provided the first focus point such that, in operation, the scan transfer device receives collimated light from the point source and transfers the two-dimensional collimated light scan from the point source into an eye accommodated at the second focus point and the light detector detects light reflected from the retina of the eye to produce an image of the retina, and wherein the axis of rotation of the one-dimensional scanning element is perpendicular or parallel to a line joining the first focus point and the second focus point of the scan transfer device and the axis of rotation of the rotatable mount is perpendicular or parallel to the line joining the first focus point and the second focus point of the scan transfer device.

17. A method of treating the retina of an eye with collimated light comprising:
providing a source of collimated light;
providing a light detector;
providing a two-dimensional scanning device comprising a one-dimensional scanning element having a first axis of rotation and a rotatable mount having a second axis of rotation, and wherein the one-dimensional scanning element is mounted to the rotatable mount and the first and second axes of rotation are orthogonal and substantially co-planar, the two-dimensional scanning device, in use, receiving collimated light from the source of collimated light;
using the source of collimated light and the two-dimensional scanning device in combination to provide a two-dimensional collimated light scan from a point source located at the intersection of the first and second axes;
providing a scan transfer device with a reflective surface, the reflective surface having a first focus point and a second focus point;
providing the point source at the first focus point of the scan transfer device and an eye at the second focus point of the scan transfer device, the scan transfer device, in use, receiving collimated light from the point source;
using the scan transfer device to transfer the two-dimensional collimated light scan from the point source into the eye; and
detecting light reflecting from the retina to produce an image of the retina, wherein the axis of rotation of the one-dimensional scanning element is perpendicular or parallel to a line joining the first focus point and the second focus point of the scan transfer device and the axis of rotation of the rotatable mount is perpendicular or parallel to the line joining the first focus point and the second focus point of the scan transfer device.

* * * * *